(12) United States Patent
De Luca

(10) Patent No.: US 8,763,667 B2
(45) Date of Patent: Jul. 1, 2014

(54) LAYERED PACKAGING CUSHION

(75) Inventor: Nicholas P. De Luca, Washington, DC (US)

(73) Assignee: Sealed Air Corporation (US), Elmwood Park, NJ (US)

( * ) Notice: Subject to any disclaimer, the term of this patent is extended or adjusted under 35 U.S.C. 154(b) by 2800 days.

(21) Appl. No.: 10/532,525

(22) PCT Filed: Oct. 31, 2003

(86) PCT No.: PCT/US03/34691
§ 371 (c)(1),
(2), (4) Date: Oct. 21, 2005

(87) PCT Pub. No.: WO2004/041659
PCT Pub. Date: May 21, 2004

(65) Prior Publication Data
US 2006/0127648 A1    Jun. 15, 2006

Related U.S. Application Data

(60) Provisional application No. 60/423,267, filed on Oct. 31, 2002.

(51) Int. Cl.
*B32B 1/00* (2006.01)

(52) U.S. Cl.
USPC ............ 156/523; 156/512; 156/513; 156/516; 156/517; 156/425; 156/256; 156/264; 156/265; 156/267; 156/145

(58) Field of Classification Search
USPC ......................................................... 156/523
See application file for complete search history.

(56) References Cited

U.S. PATENT DOCUMENTS

| | | | |
|---|---|---|---|
| 4,323,756 A | 4/1982 | Brown et al. | |
| 4,575,330 A | 3/1986 | Hull | |
| 4,596,111 A * | 6/1986 | Ambrose | 53/434 |
| 4,620,466 A * | 11/1986 | Jumel et al. | 83/177 |
| 4,752,352 A | 6/1988 | Feygin | |
| 4,929,402 A | 5/1990 | Hull | |

(Continued)

FOREIGN PATENT DOCUMENTS

| | | |
|---|---|---|
| CA | 2 236 137 | 10/1999 |
| DE | 91 16 568 U | 3/1993 |

(Continued)

OTHER PUBLICATIONS

CS Cutting Specialists. "Laser Cutting Head"; "Routing Tool Head." pp. 2-3. Located on Nov. 20, 2009 at: http://www.cuttingspecialists.com/products/toolheads.html.*

(Continued)

*Primary Examiner* — Philip Tucker
*Assistant Examiner* — Vicki Wu
(74) *Attorney, Agent, or Firm* — Daniel B. Ruble (57) ABSTRACT

A packaging cushion insert is useful for cushioning a packaged object. The insert comprises a top sheet, a bottom sheet; and a plurality of interior sheets between the top and bottom sheets. The top sheet, the bottom sheet, and the plurality of interior sheets are in stacked and laminated arrangement. The top sheet, bottom sheet, and plurality of interior sheets each comprise one or more materials selected from an air-cellular cushioning material, cellular foam material, and crumpled paper material.

19 Claims, 8 Drawing Sheets

(56) References Cited

U.S. PATENT DOCUMENTS

| | | | |
|---|---|---|---|
| 4,966,059 A * | 10/1990 | Landeck | 83/53 |
| 4,996,010 A | 2/1991 | Modrek | |
| 4,999,143 A | 3/1991 | Hull et al. | |
| 5,015,424 A | 5/1991 | Smalley | |
| 5,024,862 A * | 6/1991 | Frank | 427/264 |
| 5,088,047 A * | 2/1992 | Bynum | 700/182 |
| 5,130,064 A | 7/1992 | Smalley et al. | |
| 5,146,732 A | 9/1992 | Grey et al. | |
| 5,174,943 A | 12/1992 | Hull | |
| 5,182,055 A | 1/1993 | Allison et al. | |
| 5,192,559 A | 3/1993 | Hull et al. | |
| 5,236,637 A | 8/1993 | Hull | |
| 5,469,691 A | 11/1995 | Grey et al. | |
| 5,630,981 A | 5/1997 | Hull | |
| 5,637,169 A | 6/1997 | Hull et al. | |
| 5,637,175 A | 6/1997 | Feygin et al. | |
| 5,638,565 A | 6/1997 | Pekar | |
| 5,651,237 A * | 7/1997 | De Luca | 53/472 |
| 5,711,911 A | 1/1998 | Hull | |
| 5,730,817 A * | 3/1998 | Feygin et al. | 156/64 |
| 5,764,521 A | 6/1998 | Batchelder et al. | |
| 5,779,967 A | 7/1998 | Hull | |
| 5,814,265 A | 9/1998 | Hull | |
| 5,876,550 A | 3/1999 | Feygin et al. | |
| 5,897,825 A | 4/1999 | Fruth et al. | |
| 5,904,889 A | 5/1999 | Serbin et al. | |
| 6,036,911 A | 3/2000 | Allison et al. | |
| D423,023 S | 4/2000 | Strong et al. | |
| 6,084,980 A | 7/2000 | Nguyen et al. | |
| 6,131,376 A | 10/2000 | Grey et al. | |
| 6,139,188 A * | 10/2000 | Marzano | 383/110 |
| 6,167,790 B1 | 1/2001 | Bambara et al. | |
| 6,241,934 B1 | 6/2001 | Everett et al. | |
| 6,261,506 B1 | 7/2001 | Nguyen et al. | |
| 6,261,507 B1 | 7/2001 | Gigl et al. | |
| 6,264,873 B1 | 7/2001 | Gigl et al. | |
| 6,357,855 B1 | 3/2002 | Kerekes et al. | |
| 6,432,512 B1 | 8/2002 | Brandolini | |
| 6,520,332 B1 | 2/2003 | Barmore et al. | |

FOREIGN PATENT DOCUMENTS

| | | |
|---|---|---|
| DE | 298 04 746 U | 6/1998 |
| DE | 100 49 599 A | 5/2002 |
| EP | 0 736 278 A | 10/1996 |
| WO | WO 01/34497 A | 5/2001 |

OTHER PUBLICATIONS

ThomasNet. "Stainless Steel Waterjet Cutting Services." p. 1. Located on Nov. 20, 2009 at: http://www.thomasnet.com/products/waterjet-cutting-services-stainless-steel-96071154-1.html.*

Statocell Plus: Special Density Foam and Film Laminates, Product Brochure, Sealed Air Corporation, Dec. 1997.

Website page "Company About 3D Systems," 3D Systems Corporation Solid Imaging (printed from internet Oct. 21, 2002).

Helisys Inc. entry for European Medical Mfg Supplier Directory (printed from internet Oct. 21, 2002).

The RP&T Centre; Helisys LOM 2030 E; http://www.warwick.ac.uk/atc/rpt/Facilites/lom2030.htm (printed from internet Oct. 21, 2002).

* cited by examiner

LAYERED PACKAGING CUSHION

This application claims the benefit of U.S. Provisional Application No. 60/423,267 filed Oct. 31, 2002, which is incorporated herein in its entirety by reference.

BACKGROUND OF THE INVENTION

The present invention relates to packaging cushion inserts and methods of making them.

A packaged product may be nested into the cavities of cushioning inserts, such as foam end caps, to help protect and stabilize the packaged product inside its shipping box. The cushioning insert is preferably designed in view of the maximum shock, vibration, temperature, humidity, and load fluctuations to which the package system is expected to be exposed. A foam end cap may be made by cutting and fitting foam pieces together by hand, which leads to increased labor expenses. Alternatively, a foam end caps may formed using a mold. However, a mold also adds to the expense of forming the end cap and limits the ease of modifying the end cap design.

SUMMARY OF THE INVENTION

The present invention addresses one or more of the aforementioned problems. A packaging cushion insert, useful for cushioning a packaged object, comprises a top sheet, a bottom sheet; and a plurality of interior sheets between the top and bottom sheets. The top sheet, the bottom sheet, and the plurality of interior sheets are in stacked arrangement. The top sheet is attached to a first sheet of the plurality of interior sheets. The bottom sheet is attached a second sheet of the plurality of interior sheets. Each of the plurality of interior sheets is attached to at least one other sheet of the plurality or interior sheets. The top sheet, bottom sheet, and plurality of interior sheets each comprise one or more materials selected from an air-cellular cushioning material, cellular foam material, and crumpled paper material.

A method of making a package cushioning insert useful for cushioning an object comprising the following steps: 1) selecting the dimensions of a top sheet, a bottom sheet, and a plurality of interior sheets based on the shape of the object; 2) cutting the top sheet, bottom sheet, and plurality of interior sheets to the selected dimensions; 3) placing the top sheet, the bottom sheet, and the plurality of interior sheets in stacked arrangement with the plurality of interior sheets between the top and bottom sheets; 4) attaching the top sheet to a first sheet of the plurality of interior sheets; 5) attaching the bottom sheet to a second sheet of the plurality of interior sheets; and 6) attaching each of the plurality of interior sheets to at least one other sheet of the plurality of interior sheets. The top sheet, bottom sheet, and plurality of interior sheets comprise one or more materials selected from air-cellular cushioning material, cellular foam material, and crumpled paper material.

These and other objects, advantages, and features of the invention will be more readily understood and appreciated by reference to the detailed description of the invention and the drawings.

DETAILED DESCRIPTION OF THE INVENTION

Figure 6:
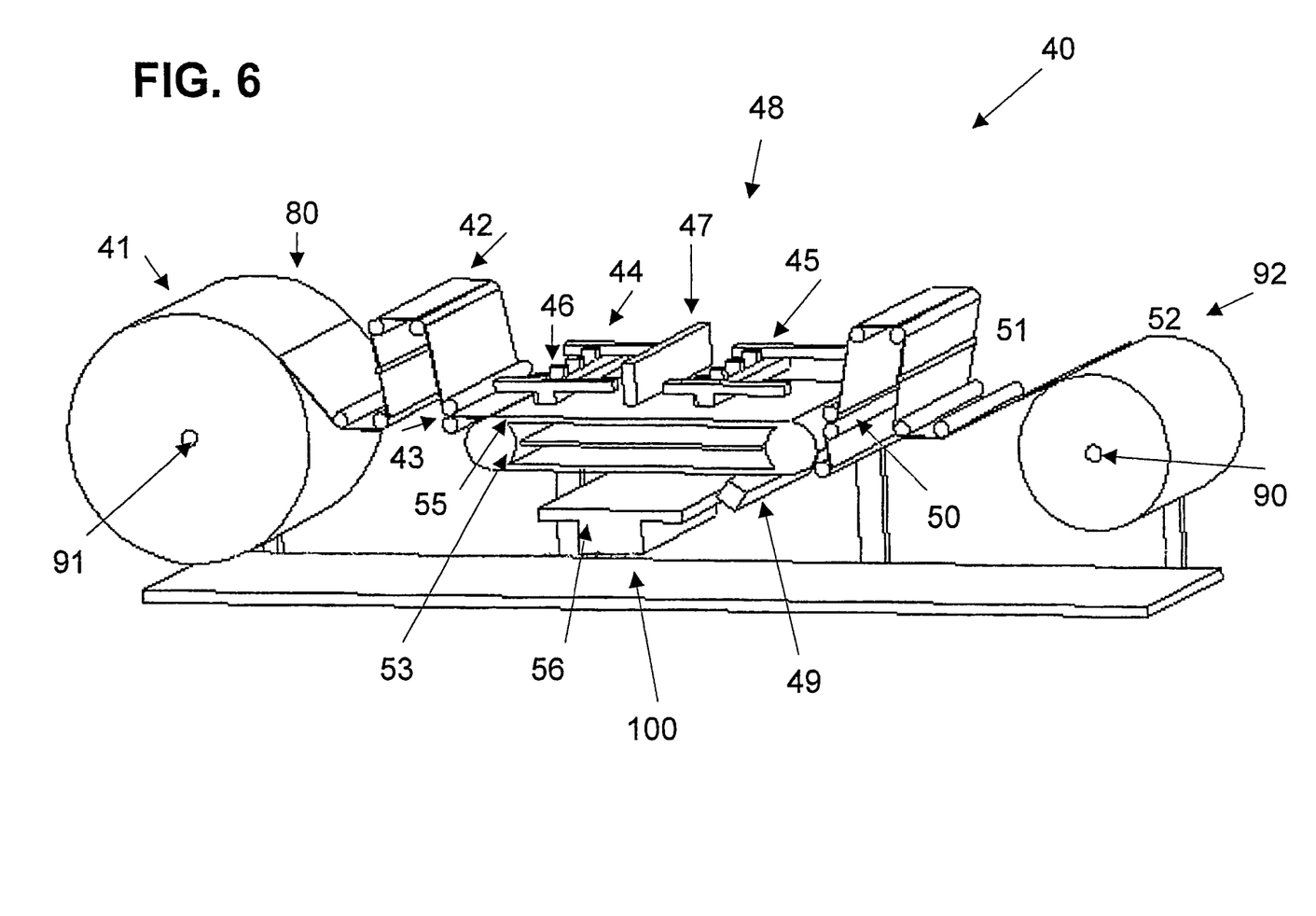
FIG. 6 is a representative perspective view of a machine useful in making the packaging insert of the present invention.
Figure 7:
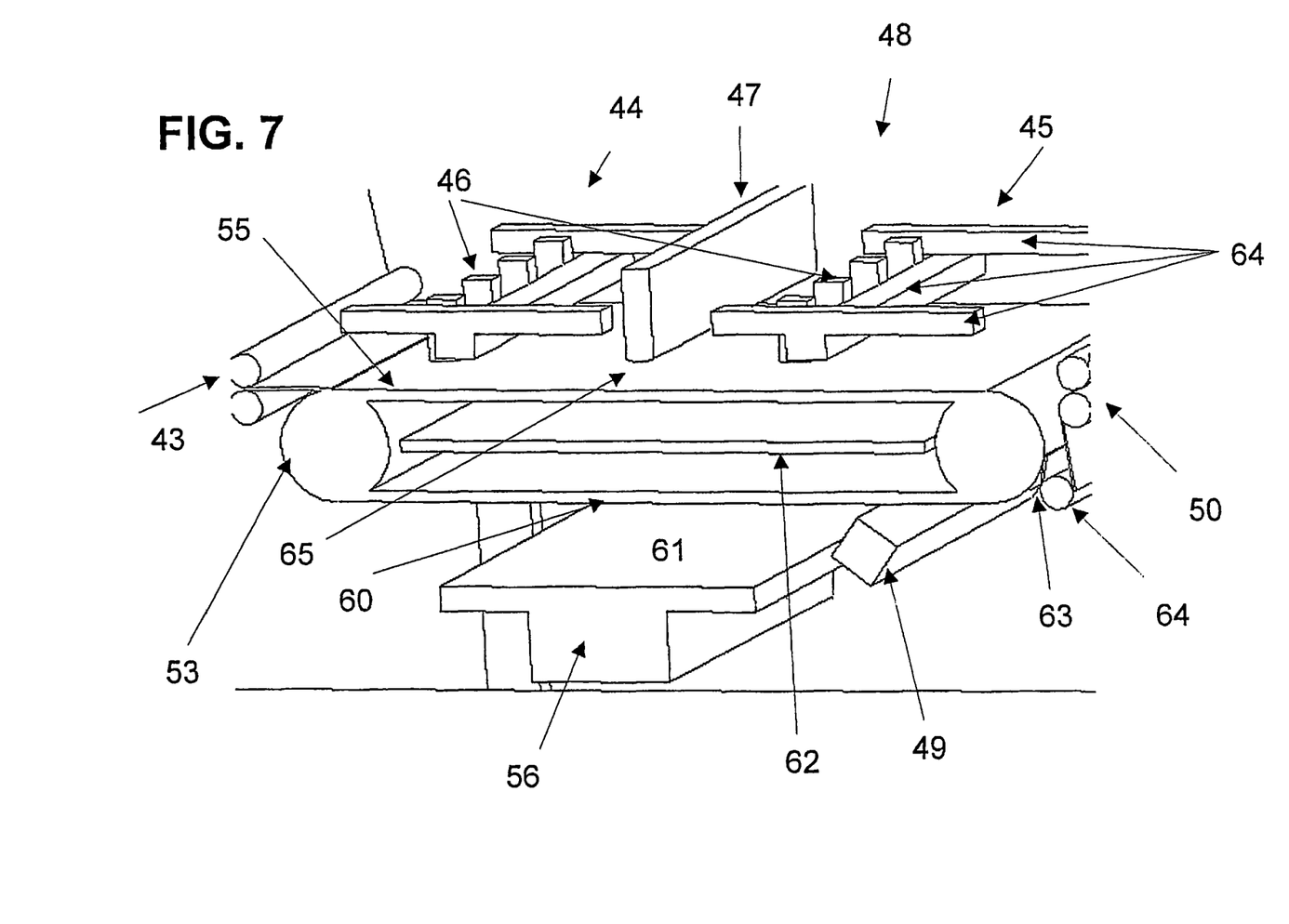
FIG. 7 is an enlarged view of a portion of FIG. 6.

A packaging cushion insert 6 (FIGS. 2-3) may be formed using the machine 40 (FIGS. 6-7).

Figure 2:
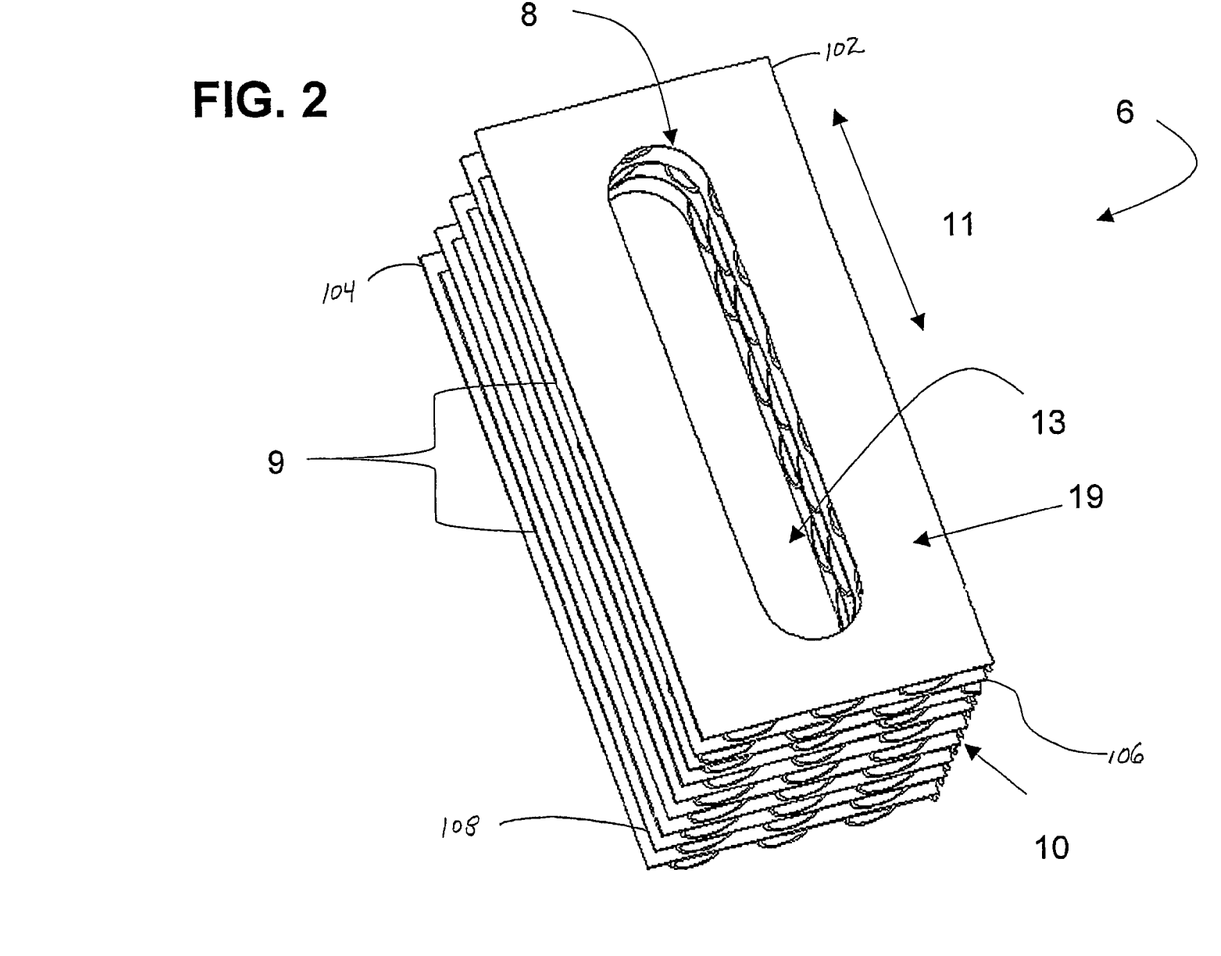
FIG. 2 is an perspective view of a packaging cushion insert of the present invention.

The packaging cushion insert 6 comprises a top sheet 102, a bottom sheet 104, and a plurality of interior sheets 106, such as first interior sheet 106 and second interior sheet 108. (FIG. 2.) The sheets are in stacked or laminated arrangement. Top sheet 102 is attached to first interior sheet 106. Bottom sheet 104 is attached to second interior sheet 108. Each of the plurality of interior sheets 9 is attached to at least one other sheet of the plurality of interior sheets. For example, other than first and second interior sheets 106, 108, each of the plurality of interior sheets is attached to two other sheets of the plurality of interior sheets. The number of interior sheets may be at least any of the following: 2, 3, 4, 5, 8, 10, 15, 20, 25, 30, 40, and 50; and may be at most any of the following: 45, 35, 30, 25, 20, 15, 12, 10, 8, 4, and 2.

Figure 3:
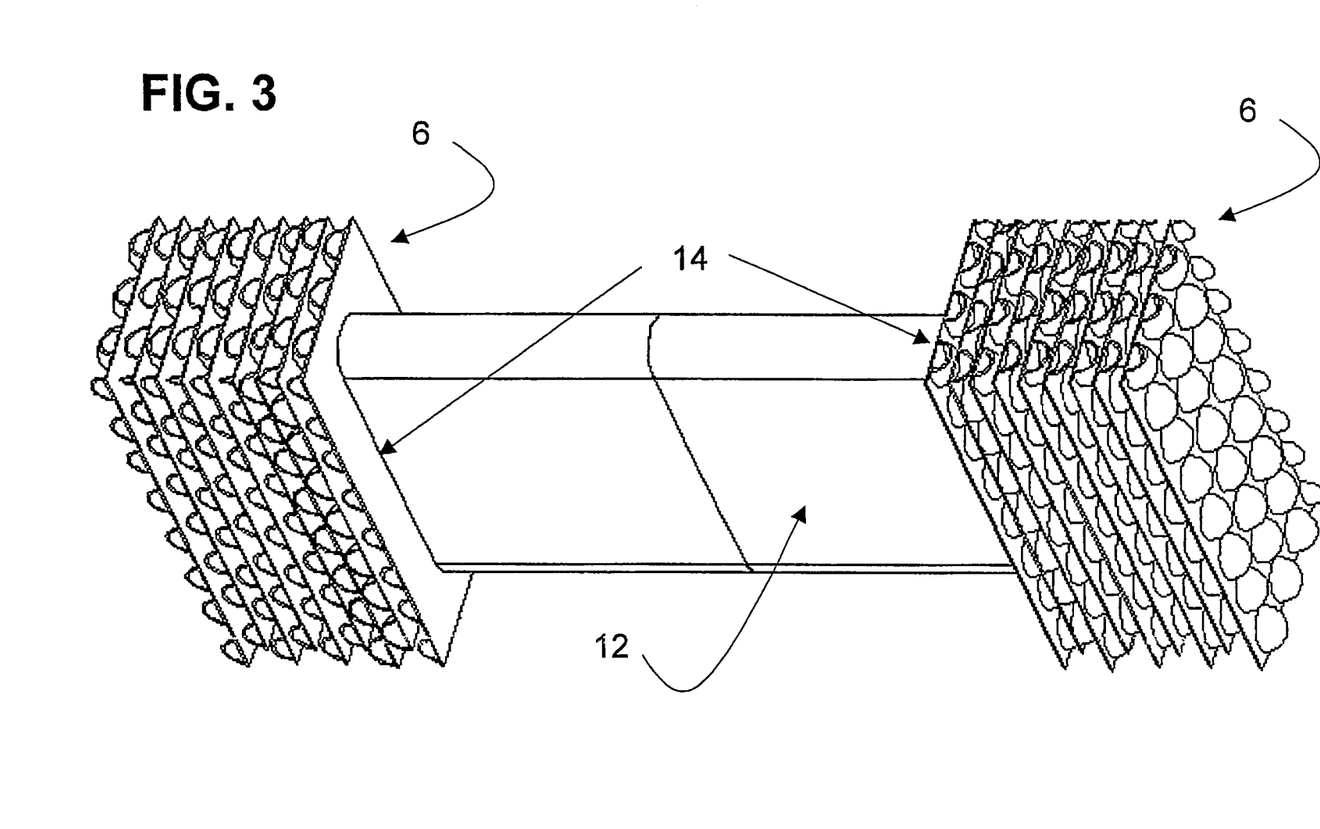
FIG. 3 is a perspective view of two of the packaging inserts of FIG. 2 installed on a an object to be packaged.

As illustrated in FIG. 2, top sheet 102, first interior sheet 104, and another of the plurality of interior sheets 9 each defines an aperture 8 to accommodate insertion of at least a portion (e.g., ends 14) of object 12 so that the insert 6 surrounds at least a portion of object 12, as illustrated in FIG. 3. At least one of top sheet 102 or bottom sheet 104 may define an aperture, and at least one of the plurality of interior sheets 9 may define an aperture, for example, to accommodate insertion of a portion of the object to be packaged. The apertures of the sheets may be in aligned arrangement as illustrated in FIG. 2 to form cavity 13 in the insert 6.

Figure 1:
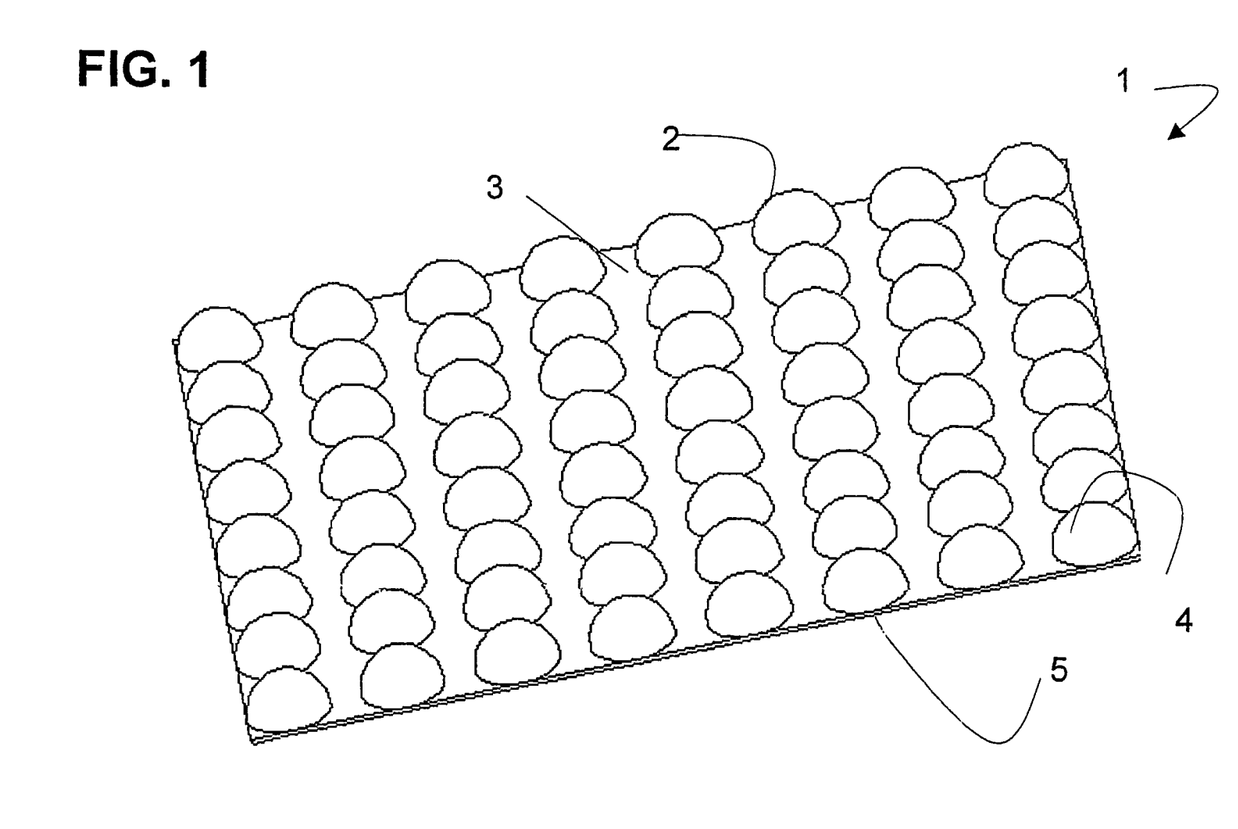
FIG. 1 is a perspective view of a sheet material useful in forming the packaging insert of the present invention.

In the embodiment illustrated in FIG. 2, the sheets comprise an air-cellular cushioning material; however, each or any of the sheets may comprise one or more materials selected from air-cellular cushioning material, cellular foam material, and crumpled paper (discussed below). Sheet 1 (FIG. 1) is a sheet of air-cellular cushioning material comprising a lamination of a top film 4 to a bottom film 5 to form air cells 2 and land areas 3. The reverse side (not shown) of sheet 1 of FIG. 1 is relatively smooth if the air cells 2 protrude from only one side of the sheet (this can be seen in FIG. 2). However, the air cells may protrude from both sides of an air-cellular sheet. The air-cellular material may comprise films comprising one or more thermoplastic polymers, such as polyethylene and nylon. Useful air-cellular materials, are disclosed in U.S. Pat. Nos. 4,314,865; 4,112,879; 4,417,936; 4,427,474; 5,116,444; and 5,665,456, each of which is incorporated herein in its entirety by reference.

A sheet may comprise cellular foam material, which may be a closed cell foam or an open cell foam. The term "closed cell" foam as used herein means that the foam comprises an open cell content of 30 volume % or less, measured according to ASTM D2856-94 (Procedure A). (For foam having a thickness of less than 0.984 inches, then the foam sample size shall be 0.984 inches by 0.984 inches by the actual average thickness of the foam.) The term "open cell" foam as used herein means that the foam comprises an open cell content of greater than 30 volume %, measured according to ASTM D2856 as set forth above. The foam material may have an average cell size of at least about any of the following values: 0.01, 0.05, 0.1, 0.5, and 1 mm. The foam may have an average cell size of at most about any of the following values: 10, 5, 3, 1, and 0.5 mm. The average cell size may be measured according to ASTM D3576-98 (Procedure A).

The density of the foam material may be at least about any of the following: 0.5, 1, 3, 5, 8, 10, 12, 15, 20, 25, 30, and 35 pounds per cubic foot (lb/ft3). The density of the foam may be at most about any of the following values: 40, 35, 30, 25, 20, and 15 lb/ft3. The density may be measured according to ASTM D3575-00, Suffix W, Test Method A, which is incorporated herein in its entirety by reference.

A sheet may comprise crumpled paper, such as that described in any of U.S. Pat. Nos. 2,882,802; 3,799,039; 4,750,896; 4,937,131; 5,203,761; 5,322,477; and 5,891,009, each of which is incorporated in its entirety by reference.

The average thickness of a sheet material may be at least about any of the following: 1, 5, 10, 15, 20, 25, 30, 35, 40, 45, 50, 55, 60, 65, 70, 75, 80, 85, 90, 95, and 100 mils. Further, the average thickness of a sheet may be at least about any of the following: 0.2, 0.25, 0.3, 0.35, 0.4, 0.5, 0.75, and 1 inches. The average thickness of a sheet may be at most about any of the following values: 200, 195, 190, 185, 180, 175, 170, 165, 160, 155, 150, 145, 140, 135, 130, 125, 120, 115, 110, 105, 100, 95, 90, 85, 80, 75, 70, 65, 60, 55, 50, 45, 40, 35, 30, and 25 mils. Further the average thickness of a sheet may be at most about any of the following values: 4 inches, 3.5 inches, 3 inches, 2.5 inches, 2 inches, and 1.5 inches. The thickness of an air cellular sheet is measured from the top of the air cells 2 to the reverse side of the sheet. The thickness of a crumpled paper sheet is measured while the sheet is in the crumpled condition.

A sheet preferably exhibits a flexural modulus sufficient to withstand the expected handling and use conditions. The flexural modulus of a sheet may be at most about any of the following values: 4,000; 3,000; 2,500; 2,000; 1,900; 1,800; 1,700; 1,500; 1,200; 1,100; 1,000; 900; 800; 700; 600; and 500 psi. The flexural modulus of a sheet may be at least about any of the following values: 800; 900; 1,000; 1,100; 1,200; 1,700; 1,800; 1,900; 2,000; 2,200; 2,500; and 3,000 psi (pounds/square inch). The flexural modulus (i.e., the tangent modulus of elasticity in bending) may be measured in accordance with ASTM D790-00 (Procedure A or B, depending on the nature of the sheet, as set forth in the ASTM test), which is incorporated herein in its entirety by reference. If the sheet is so flexible that it is difficult to run the above ASTM test procedure to calculate the flexural modulus (e.g., a sheet with a flexural modulus of less than about 1,000 psi), then the ASTM test may be modified by using a higher "Z" (i.e., rate of straining) and/or stacking several samples of the sheet together (taping the sample ends together) to run the test.

Each sheet may be directly attached to its adjacent sheet. A sheet may be adhesively attached or may be attached by one or more heat seals.

The shape of insert 6 may be formed from the sheets laminated at any angle relative to top surface 19. This allows maximized use of isotropic characteristics of a sheet. In the case of cushion insert 6 of FIG. 2, sheet 102 lies at a 0 degree offset in the x, y, and z directions relative to top surface 19. Cushioning insert 6 may comprise sheets of differing materials.

The adhesion of one sheet to the next is done at the interface 10 area along the planer surface 11. The adhering at interface 10 may be made by adhesives, heat seals, or mechanical means, such as hook and loop.

Figure 4:
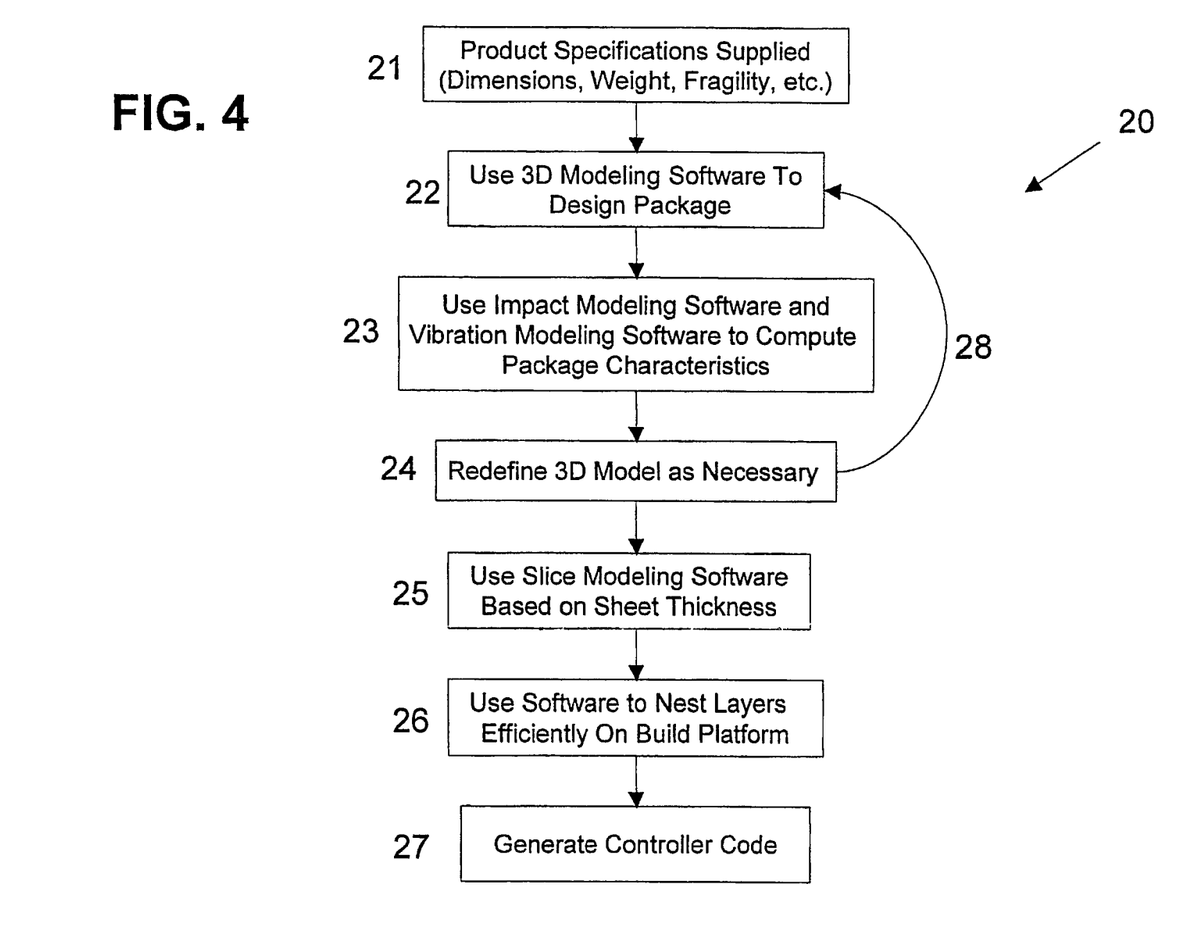
FIG. 4 is a flowchart describing steps useful in a process of making the cushion insert of the present invention.

FIG. 4 illustrates a process flow-chart 20 useful in designing and developing a packaging cushion insert of the present invention. The process by which the sheets are cut and then assembled may begin by using a three dimensional computer modeling system to create the form of the cushion insert. Such modeling may also employ finite element analysis software and impact simulation software to determine the proper design of the package. Once modeled, the mathematical computer representation of the cushion insert may be sectioned to represent individual layers for cutting; such layers, potentially, being of different thicknesses or different material. The full representation of these sections may be sent to a computer numerically controlled code generator that defines the path for a cutting tool; such code varying depending on the number of sheets to be simultaneously cut. Such code may also create two separate tool paths for the interior and exterior boundaries of each sheet of the insert. The code may also adjust for the use of an intermittent or continuous flow of sheet stock.

In first step 21 of process 20, the dimensions and overall features of an object to be packaged are provided to a designer; these include weight, overall dimensions, vibration constraints, and maximum allowable acceleration data. The International Safe Transit Association (ISTA) provides additional guidelines for minimum compliance standards for shipped packages. A computer model of the product itself may be useful to the designers. Using this information, in the next step 22, the package cushion may be designed in accordance with any exterior shipping container constraints using a three dimensional computer aided design (CAD) program.

The third step 23 of process 20, a finite element analysis program is used to test the product, cushion, and exterior container system. Such a program may model a dynamic situation, allowing for both vibration and drop testing simulation. In addition, the isotropic properties of the sheet structure (as discussed earlier in reference to FIG. 2) may be integrated into the program to allow designers to vary the orientation of the cushion to maximize the beneficial characteristics of the sheets in a particular x, y, or z direction. After using the software of step 23, the cushion insert design may be further modified in step 24; this cycle 28 being repeated until a solution is found.

Figure 5:
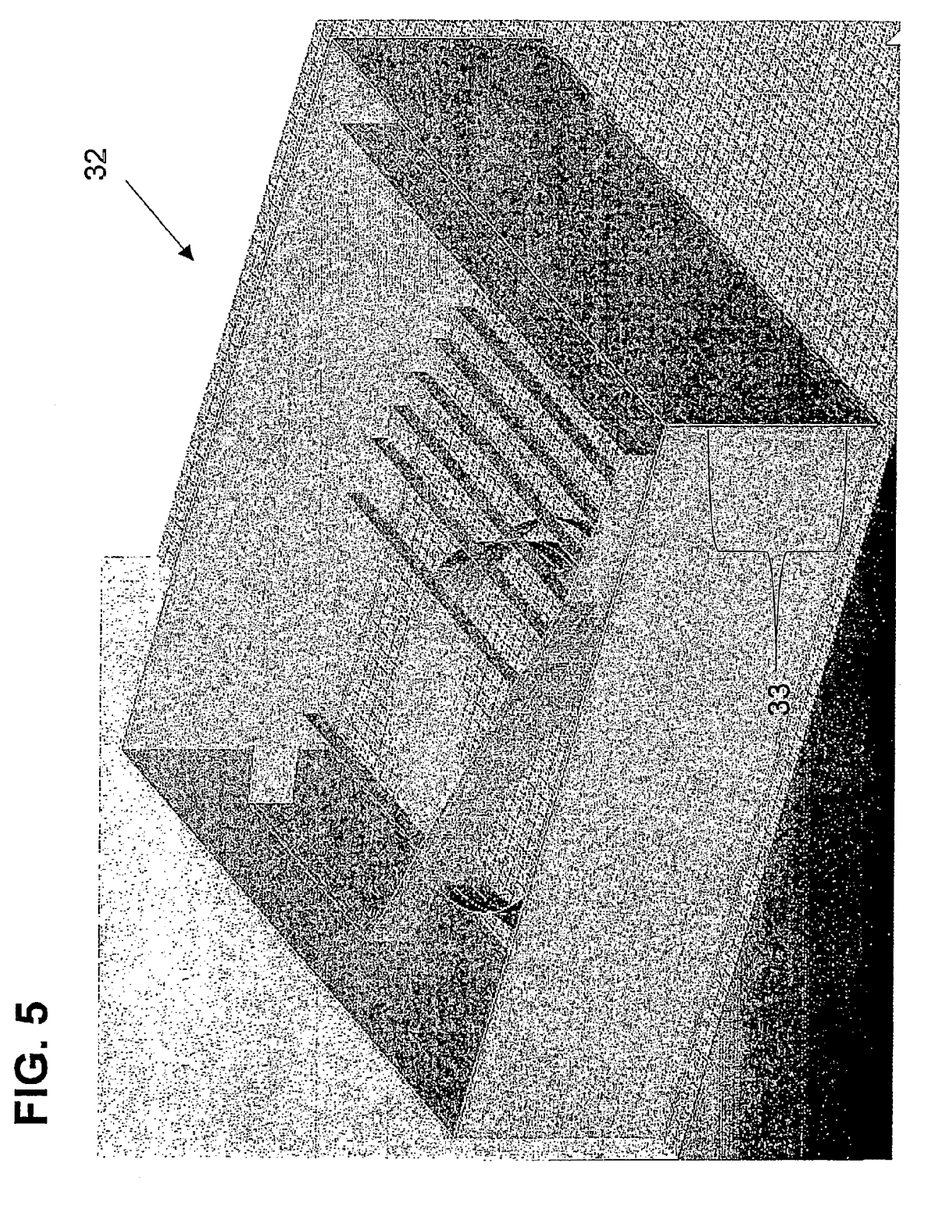
FIG. 5 is a representative perspective view of an object packaged with a cushioning insert of the present invention.

Step 25 of process 20 involves using slicing software to cut the model into the respective layers needed to create a cushion insert. The model may be oriented in the program in such a manner that sectioning may be done in the same way intended during the design cycle 28. The software may incorporate input data on sheet thickness and sheet material characteristics (e.g., expected compression factor expected for each sheet material). FIG. 5 illustrates the model 32 of a cushion insert that has been sectioned into layers 33.

In step 26 of process 20 (FIG. 4), the size of the cutting bed on which the layers are eventually cut may be taken into consideration in order to maximize efficient use of the material. While step 26 may generally be accomplished using stand-alone software, software used in the prior step 25 may also incorporate this item.

In order to minimize the costs associated with the production system illustrated in FIG. 6, several parameters pertaining to the nesting step 26 may be held constant. Specifically, although rotating individual layers of a part may be considered an important element of nesting (especially when creating non-rectangular layers), rotating may be avoided (or rotation always set at 0 degrees) as otherwise rotating stacker units at 56, described hereafter in FIGS. 6 and 7, would be required. In addition, the repetition of parts, in the direction perpendicular to the sheet feed direction, may be held constant in the software for each particular cushion. This avoids having to manually move or install motorized movers for the cutting heads 46 described hereafter in FIG. 6. Regarding the sequence in which the parts are cut, such a sequence preferably creates multiple layers of the same shape from a single sheet rather than multiple different layers of the same cushion. For example with respect to a cushion consisting of 30 layers, each 10 inches wide, being cut from a base sheet 42" wide, rather than cutting layers 1-4 across the sheets leaving 2" on the side), it may be preferable to cut layer 1 four times. Subsequently, layer 2 will be cut four times, and so on; thus producing four parts at a time.

The outputs of step 26 include the following items: 1) the shape of the cutting path required to form both the exterior and the interior cutout portions of each layer; this shape incorporating multiple parts of possible, 2) the number of cushions repeated in the direction perpendicular to the sheet travel direction, 3) the repeat length of the sheet in the direction along the sheet movement.

Using the data output of step six, a numerical code generation program may be used for the final step 27 of process 20 in FIG. 4. This code may be used to create instructions for the control of the servo motors and other actuators used for feeding, cutting, and stacking processes of machine 40 described in FIGS. 6 and 7. Software packages available for this custom programming process are know to those of skill in the art. The final program output may be uploaded to machine 40 to allow for creation of the cushion inserts.

FIG. 6 discloses the main elements of a production machine 40 useful to make packaging cushion inserts of the present invention. The machine 40 used to create the cushion inserts may employ a source of raw sheet stock, a controlled film advance section, a moveable or conveyor based cutting platform with adjustable cutters, a scrap separation station, an adhesive or heat application station, a movable and conveyor based stacking station, a sheet removal, compression, and storage system and a staging area for packing items using the produced cushions, as illustrated in FIGS. 6-7 as described below.

The source of sheet stock may be in the form of a prefabricated roll 41. The raw material may be produced at the same site of that at which production of the cushion inserts is done, and therefore, the material may be directed to the location of roll 41 in area 80. The sheet material may be of a continuous structure as shown by roll 41, or it may be provided in individual portions being perforated periodically, with the roll unwinder 91 feeding system disclosed herein at 80 being changed accordingly.

Area 42 is a tensioning system used to control the force applied to the sheet material, prior to the sheet engaging the feed nip roller 43. The nip 43 advances the sheet onto the top surface 55 of conveyor 53, that then moves the correct repeat amount under cutting area number 1, designated as 44. Conveyor 53 may have a vacuum system attached to it used to create a strong suction on surface 55 and 60 in FIG. 7, and is also compatible with the cutting method used by the cutting heads 46. In the case of using a waterjet cutting system, such a conveyor belt would be made of a rectangular thin-walled metal honeycomb like structure, with an absorbing panel or blocking panel 62 to prevent the cutting fluid from penetrating to the opposite side 60 of belt 53.

In area 44 cutting heads 46 move along rails 64 to create the cut lines representing the exterior perimeter of the inner cutouts of each layered section. Vacuum head 47 located on top of the sheet material then removes the cut inner areas. Vacuum head 47 may move in conjunction with the cutting heads 46 in area 44 or may rest in a fixed position between cutting areas 44 and 45. In addition, the vacuum pressure of 47 is adjusted to compensate for the vacuum pulling from the conveyor belt 53. Also, the vacuum from conveyor, belt 53 may be blocked just under the vacuum head 47 at 65 in FIG. 7 so that an increase in the pull-off pressure from 47 is generated.

In the second cutting area 45, the exterior perimeter of the shaped layers is cut. As in area 44, the number of cutting heads positioned to correspond the repetition of the parts across the sheet (in the direction perpendicular to the sheet travel). As mentioned earlier, it is most economical to position these manually. In some cases, a single set of cutting heads can be used for both cutting areas 44 and 45 with the vacuum head 47 activating only in area 44.

Separation of the scrap material of roll 41 from the sheets cut in area 45 occurs at area 63 in FIG. 7 as the waste raw stock peels away and bends around roller 64 and enters nip 50 as the layers continue along the bottom surface 60 of conveyor 53. Nip 50 can also be used to crush the scrap material tightly to remove air pockets, thus acting as a compactor. In the case where the scrap material is rolled, a tension system at 51 and a rewinder 90 forms roll 52. In area 90, a large collection bin or a fan folding system may also be used; such collection systems designed to maximize the efficiency with which waste material may be collected for reuse or recycling.

The cut sheets on the bottom surface 60 of conveyor 53 pass under a heat, gluing, or adhering station 49 and then are pressed against the layers resting on surface 61 by the upward movement of the stacker unit 56. The stacker unit moves through automatic means, along the conveyor path in order to adjust for the repeat length of the layers. The base surface 61 of stacker 56 may consist of a conveyor belt that activates upon completion of the units and transports them to a collection area 100. At collection area 100 completed cushion inserts may be placed into collection bins or packed directly onto products to be shipped using automatic or manual means.

Figure 8:
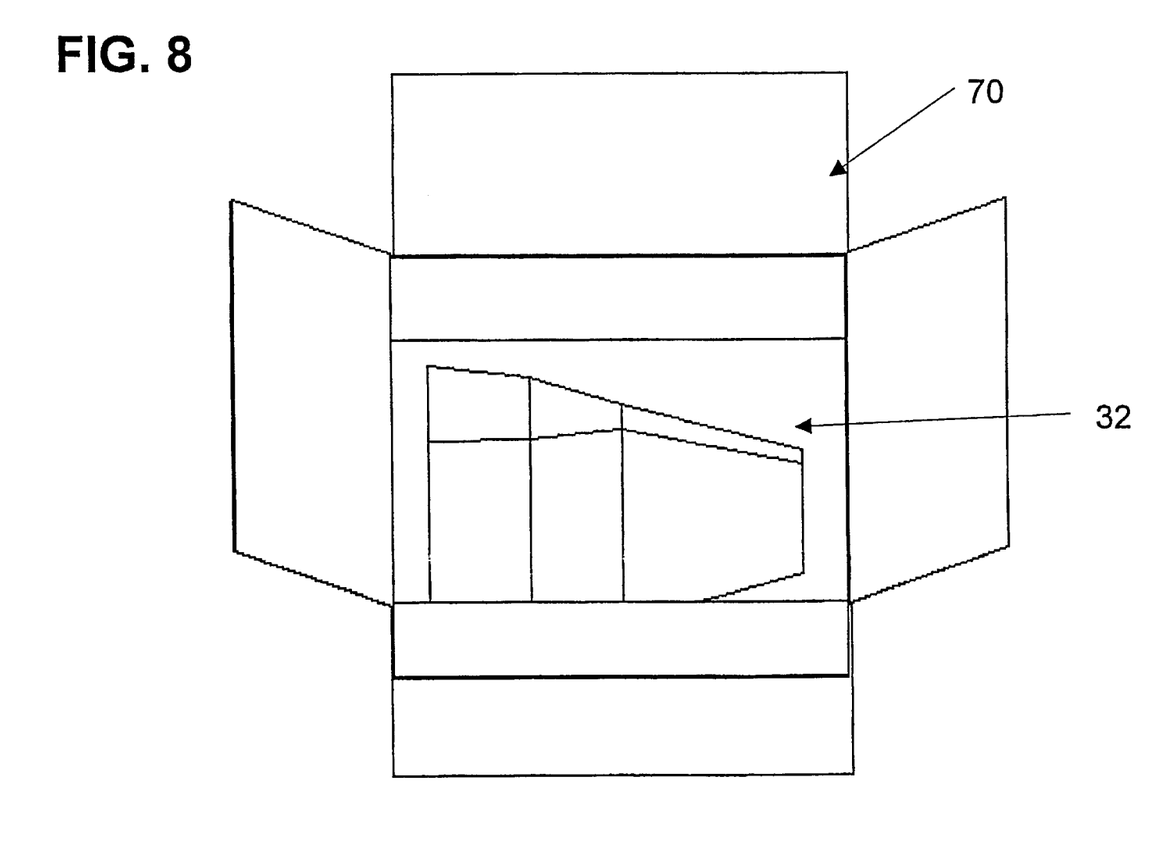
FIG. 8 is representative perspective view of the packaging cushion insert of the present invention in a box.

FIG. 8 illustrates the combination of a layered cushion insert 32, also shown in FIG. 5, in combination with a shipping carton 70. Integration of unit 32 with other exterior shipping containers such as envelopes is possible and may be done manually or automatically in area 100 of FIG. 6.

Any numerical values recited herein include all values from the lower value to the upper value in increments of one unit provided that there is a separation of at least 2 units between any lower value and any higher value. As an example, if it is stated that the amount of a component or a value of a process variable (e.g., temperature, pressure, time) may range from any of 1 to 90, 20 to 80, or 30 to 70, or be any of at least 1, 20, or 30 and at most 90, 80, or 70, then it is intended that values such as 15 to 85, 22 to 68, 43 to 51, and 30 to 32, as well as at least 15, at least 22, and at most 32, are expressly enumerated in this specification. For values that are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

The above descriptions are those of preferred embodiments of the invention. Various alterations and changes can be made without departing from the spirit and broader aspects of the invention as defined in the claims, which are to be interpreted in accordance with the principles of patent law, including the doctrine of equivalents. Except in the claims and the specific examples, or where otherwise expressly indicated, all numerical quantities in this description indicating amounts of material, reaction conditions, use conditions, molecular weights, and/or number of carbon atoms, and the like, are to be understood as modified by the word "about" in describing the broadest scope of the invention. Any reference to an item in the disclosure or to an element in the claim in the singular using the articles "a," "an," "the," or "said" is not to be construed as limiting the item or element to the singular unless expressly so stated. All references to ASTM tests are to the most recent, currently approved, and published version of the ASTM test identified, as of the priority filing date of this application. Each such published ASTM test method is incorporated herein in its entirety by this reference.

What is claimed is:

1. A machine for making a packaging cushion insert from sheet stock of cushioning material, the machine comprising:
    a conveyor adapted to movably support the sheet stock and sequential discrete sheets of desired shapes;
    one or more fluid jet cutting heads movable transversely and longitudinally relative to the conveyor and adapted to cut the sheet stock supported by the conveyor into the discrete sheets; and
    a platform below the conveyor adapted to receive the discrete sheets from the conveyor, wherein the platform and conveyor are movable relative each other:
        i) to place the discrete sheets in stacked arrangement on the platform when receiving the discrete sheets from the conveyor; and
        ii) to compress the stacked arrangement of discrete sheets between the platform and the conveyor to produce the packaging cushion insert.

2. The machine of claim 1 further comprising a computerized controller for controlling the movements of the conveyor, the one or more cutting heads, and the platform.

3. The machine of claim 1 wherein the conveyor comprises a vacuum conveyor.

4. The machine of claim 1 further comprising an adhesion station upstream from the platform and adapted to apply an adhesive to the discrete sheets.

5. The machine of claim 1 further comprising a heating station upstream from the platform and adapted to heat the discrete sheets.

6. A machine for making a packaging cushion insert from sheet stock of cushioning material, the machine comprising:
    a conveyor adapted to movably support the sheet stock and sequential discrete sheets of desired shapes;
    one or more cutting heads movable transversely and longitudinally relative to the conveyor and adapted to cut the sheet stock supported by the conveyor into the discrete sheets, wherein the one or more cutting heads comprise:
        a first set of one or more cutting heads movable transversely and longitudinally relative to the conveyor and adapted to cut inner scrap cutouts from the sheet stock supported by the conveyor; and
        a second set of one or more cutting heads movable transversely and longitudinally relative to the conveyor and adapted to cut the sheet stock supported by the conveyor into sequential discrete sheets of desired shapes, wherein the second set of one or more cutting heads is downstream from the first set of one or more cutting heads;
    a platform below the conveyor adapted to receive the discrete sheets from the conveyor, wherein the platform and conveyor are movable relative each other:
        i) to place the discrete sheets in stacked arrangement on the platform when receiving the discrete sheets from the conveyor; and
        ii) to compress the stacked arrangement of discrete sheets between the platform and the conveyor to produce the packaging cushion insert; and
    a vacuum head adapted to lift the inner scrap cutouts from the conveyor, wherein the vacuum head is downstream from the first set of one or more cutting heads and upstream from the second set of one or more cutting heads.

7. The machine of claim 1 wherein the one or more cutting heads are movably supported above the conveyor by rails.

8. A machine for making a packaging cushion insert from sheet stock of cushioning material, the machine comprising:
    a conveyor adapted to movably support the sheet stock and sequential discrete sheets of desired shapes;
    a plurality of cutting heads movable transversely and longitudinally relative to the conveyor and adapted to cut the sheet stock supported by the conveyor into the discrete sheets, wherein the plurality of cutting heads are adapted to cut multiple sheets of the same shape oriented across the conveyor perpendicular to the direction of travel of the conveyor; and
    a platform below the conveyor adapted to receive the discrete sheets from the conveyor, wherein the platform and conveyor are movable relative each other:
        i) to place the discrete sheets in stacked arrangement on the platform when receiving the discrete sheets from the conveyor; and
        ii) to compress the stacked arrangement of discrete sheets between the platform and the conveyor to produce the packaging cushion insert.

9. The machine of claim 1 wherein the platform is movable upwardly toward the conveyor to compress the stacked arrangement of discrete sheets between the platform and the conveyor to produce the packaging cushion insert.

10. The machine of claim 1 further comprising a sheet stock feeding system upstream of the conveyor.

11. The machine of claim 10 wherein the sheet stock feeding system is adapted to supply a continuous sheet of sheet stock of cushioning material to the conveyor.

12. The machine of claim 10 wherein the sheet stock feeding system is adapted to supply individual portions of sheet stock of cushioning material to the conveyor.

13. A machine for making a packaging cushion insert from sheet stock of cushioning material, the machine comprising:
    a conveyor adapted to movably support the sheet stock;
    one or more cutting heads movable transversely and longitudinally relative to the conveyor to define a cutting area over the conveyor, and adapted to cut the sheet stock in the cutting area over the conveyor while the sheet stock is supported by the conveyor into sequential discrete sheets of desired shapes; and
    a platform adapted to receive the discrete sheets from the conveyor, wherein the platform and conveyor are movable relative each other:
        i) to place the discrete sheets in stacked arrangement on the platform when receiving the discrete sheets from the conveyor; and
        ii) to compress the stacked arrangement of discrete sheets to produce the packaging cushion insert.

14. The machine of claim 13 wherein the platform and conveyor are movable relative each other to compress the stacked arrangement of discrete sheets between the platform and the conveyor to produce the packaging cushion insert.

15. The machine of claim 13 wherein the conveyor comprises a vacuum conveyor.

16. A machine for making a packaging cushion insert from sheet stock of cushioning material, the machine comprising:

a plurality of cutting heads movable transversely and longitudinally relative to the sheet stock and adapted to cut the sheet stock into discrete sheets of desired shapes;

a conveyor belt adapted to movably support the discrete sheets, wherein the plurality of cutting heads are adapted to cut multiple sheets of the same shape oriented across the conveyor belt perpendicular to the direction of travel of the conveyor belt; and a platform adapted to receive the discrete sheets from the conveyor belt, wherein the platform and conveyor belt are movable relative each other:
  i) to place the discrete sheets in stacked arrangement on the platform when receiving the discrete sheets from the conveyor belt; and
  ii) to compress the stacked arrangement of discrete sheets to produce the packaging cushion insert.

17. The machine of claim 16 wherein the platform is below the conveyor belt.

18. The machine of claim 16 wherein the platform and conveyor belt are movable relative each other to compress the stacked arrangement of discrete sheets between the platform and the conveyor belt to produce the packaging cushion insert.

19. The machine of claim 16 wherein the plurality of cutting heads comprise fluid jet cutting heads.

* * * * *